United States Patent [19]
Lapointe et al.

[11] Patent Number: 5,919,127
[45] Date of Patent: Jul. 6, 1999

[54] OVIDUCTAL CATALASE BINDING TO THE MEMBRANES OF SPERMATOZOA AND USES THEREOF

[75] Inventors: Serge Lapointe, St-Nicolas; Marc-André Sirard, Breakeyville, both of Canada

[73] Assignee: Universite Laval, Quebec, Canada

[21] Appl. No.: 08/802,271

[22] Filed: Feb. 19, 1997

[51] Int. Cl.[6] .............................. A61B 17/43; C12N 5/00
[52] U.S. Cl. ................................... 600/35; 435/2
[58] Field of Search .................................. 435/2, 3, 4, 6; 424/531, 561; 600/35, 33; 128/898

[56] References Cited

PUBLICATIONS

Parrish JJ et al., 1988, *Biol. Reprod.*, 38:1171–1180.
Alvarez JG et al., 1987, *J. Androl.*, 8:338–348.
Aitken RJ, 1994, *Reprod. Fertil. Dev.*, 6:19–24.
Aitken RJ, 1995, *Reprod. Fertil. Dev.*, 7:659–668.

*Primary Examiner*—David J. Isabella
*Attorney, Agent, or Firm*—Klauber & Jackson

[57] ABSTRACT

The present invention relates to a novel oviductal catalase having a molecular weight of about 60 KDa and which binds to a spermatozoa membrane outer surface, wherein said catalase once bound to the spermatozoa membrane outer surface protects said spermatozoa against oxidation. A method of stabilizing spermatozoa membrane and improving spermatozoa survival during migration in oviduct and/or uterus for artificial insemination; which comprises coating spermatozoa with such a catalase enzyme. A method of improving spermatozoa survival during migration in oviduct and/or uterus in cases of female infertility due to the absence of endogenous catalase in the genital tract of the female subject; which comprises administering catalase in the female genital tract before coït or coating spermatozoa with a catalase enzyme for artificial insemination. Also provided herein are method of diagnostic of male or female infertility.

10 Claims, 5 Drawing Sheets

OVIDUCTAL CATALASE BINDING TO THE MEMBRANES OF SPERMATOZOA AND USES THEREOF

BACKGROUND OF THE INVENTION (a) Field of the Invention

The invention relates to an oviductal catalase having a molecular weight of about 60 KDa as determined by SDS-page electrophoresis under denaturing conditions and which binds to a spermatozoa membrane outer surface, uses thereof for protection and/or preservation of spermatozoa; uses thereof in artificial insemination, and a method of diagnostic of male or female infertility.

(b) Description of Prior Art

Artificial insemination (AI) has changed the face of the dairy industry. Faster genetics improvement of a herd by use of high quality bull semen is now possible, at reasonable cost, for any farmer. This is feasible by using cryopreservation by which a single bull can inseminate thousands of cows. However, during the cryopreservation process the sperm undergo several tremendous changes in cell volume. Such massive shrinkage and swelling leads to ultrastructural changes in the sperm membranes, increasing their permeability, ultimately resulting in enzyme leakage and the accumulation of intracellular calcium. Even with the best preservation techniques to date, post-thaw survival is restricted to about 50% of the sperm population. Moreover, most surviving spermatozoa have characteristics which distinguish them from spermatozoa before cryopreservation. As a consequence, the functions of cryopreserved sperm are limited, as expressed by their reduced motility, viability and fertility in vivo, which can be only partially compensated by inseminating greater numbers of live spermatozoa. In fact, to obtain a normal fertility rate, the insemination must be performed with a minimum of $6 \times 10^6$ motile sperm per straw after thawing ($\sim 12 \times 10^6$ total), compared to only $2.5 \times 10^6$ motile fresh sperm.

Sperm quality is strongly related to free radical action and the protection provided by endogenous antioxidants. Over time, the loss of sperm motility in the rabbit and human is correlated with spontaneous lipid peroxidation (Alvarez J G et al., 1987, *J. Androl.*, 8:338–348). It has also been reported that superoxide dismutase activity (SOD) activity is a good predictor of the lifetime of a human sperm sample (Alvarez J G et al., 1987, *J. Androl.*, 8:338–348), and that total cellular SOD can be conveniently measured by sperm surface SOD activity. Indeed, a growing body of evidence indicates that a significant factor in human male infertility involves a loss of sperm function as a consequence of oxidative stress (Aitken R J, 1994, *Reprod. Fertil. Dev.*, 6:19–24). Furthermore, fresh bull semen of lower quality (<70% motile sperm) has lower antioxidant activity than in normal semen. However, the byproduct of SOD action is the production of hydrogen peroxide ($H_2O_2$). Hydrogen peroxide is a highly reactive oxygen species which is one of the most toxic compound to sperm. $H_2O_2$ could be a major player in the death of sperm in the female genital tract.

It would be highly desirable to be provided with a catalase which binds to a spermatozoa membrane outer surface to protect the spermatozoa against oxidation by $H_2O_2$.

SUMMARY OF THE INVENTION

One aim of the present invention is to show that oviductal catalase reverses the decreased motility of bovine sperm in culture medium containing specific amino acids (AA). Since those AA are found in the bovine uterus as well than the oviduct, $H_2O_2$ could be a major player in the death of sperm in the female genital tract. Catalase catalyze the decomposition of $H_2O_2$ in water and oxygen, thus breaking the chain reaction of free radical production (Aitken R J, 1995, *Reprod. Fertil. Dev.*, 7:659–668). Reactive oxygen species, such as $H_2O_2$, lead to lipid peroxidation, and that process could be the limiting factor of the lifetime of mammalian spermatozoa in the oviduct (Alvarez J G et al., 1987, *J. Androl.*, 8:338–348). Although components of oviductal fluid, or supernatants of in vitro oviductal culture promote sperm survival, in humans, horses, and cattle, the mechanism by which the oviduct maintain sperm viability is not known.

We report here a catalase activity in the bovine oviductal fluid which varies during the estrous cycle. Immunoaffinity column against human erythrocytes catalase, or direct addition of the antibody, did remove all catalase activities from the oviductal fluid. Indirect immunostaining of spermatozoa incubated in the oviductal fluid revealed an intense brown staining on the acrosomal cap. Since $H_2O_2$ is a key product in the chain reaction of free radical production which leads to lipid peroxidation, this new catalase enzyme of the present invention may be the foremost important product of the female tract for sperm survival.

In accordance with the present invention there is provided an oviductal catalase having a molecular weight of about 60 KDa as determined by SDS-page electrophoresis under denaturing conditions and which binds to a spermatozoa membrane outer surface, wherein the catalase once bound to the spermatozoa membrane outer surface protects the spermatozoa against oxidation.

In accordance with the present invention there is provided a method of stabilizing spermatozoa membrane and improving spermatozoa survival during migration in oviduct and/or uterus for artificial insemination; which comprises coating spermatozoa with a catalase enzyme.

In accordance with the present invention, the catalase enzyme may be isolated from a biological source or is recombinantly produced. The catalase enzyme may be isolated from oviduct (Fallopian tubes) and cervical mucus of human, bovine, caprine, equine, bovine or porcine origin.

In accordance with the present invention, the spermatozoa may be of bovine, caprine, equine, ovine, porcine, canine, feline, primate, pachyderm or human origin.

In accordance with the present invention there is provided a composition of spermatozoa for artificial insemination with stabilized spermatozoa membrane and improved spermatozoa survival during migration in oviduct and/or uterus, which comprises spermatozoa coated with a catalase enzyme with or without an agent preventing lipid peroxidation.

The coated spermatozoa of the composition may be frozen.

The agent preventing lipid peroxidation of the composition may be selected from the group consisting of Vitamin E (α-tocopherol), Vitamin C (ascorbic acid), pyruvate, glutathion, uric acid, taurine, albumine, DMSO, superoxid dismutase (SOD), catalase (from many sources) and lactoferrin.

In accordance with the present invention there is provided a method of diagnostic of low fertility or infertility in a male subject; which comprises the steps of:

a) incubating spermatozoa obtained from the male subject with a catalase enzyme or with biological fluid containing a catalase enzyme; and b) determining the presence of catalase on spermatozoa membrane; whereby the incapacity of spermatozoa to bind to catalase is indicative of infertility of the subject.

In accordance with the present invention there is provided a method of diagnostic of low fertility or infertility in a female subject; which comprises the step of determining the absence or presence of an oviductal catalase in oviductal fluid and/or cervical mucus obtained from the subject; whereby the absence of catalase is indicative of infertility of the subject.

In accordance with the present invention, the determination of the presence of catalase may be effected using an anti-catalase antibody directly or indirectly detected.

In accordance with the present invention there is provided a method of improving spermatozoa survival during migration in oviduct and/or uterus in cases of female infertility due to the absence of endogenous catalase in the genital tract of the female subject; which comprises administering catalase in the female genital tract before coït or coating spermatozoa with a catalase enzyme for artificial insemination.

DETAILED DESCRIPTION OF THE INVENTION

Hydrogen peroxide ($H_2O_2$) is a highly reactive oxygen species which is one of the most toxic compound to sperm. $H_2O_2$ not only inhibit the livability, but also the acrosome reaction, the sperm binding with the egg and oocyte penetration. The oviductal catalase of the present invention activates the decomposition of $H_2O_2$ in water and oxygen, thus breaking the chain reaction of free radical production leading to lipid peroxidation. The catalase activity in oviductal fluid increased during the cycle, to reach its maximal activity just before ovulation (days 18–20). No significant difference in the activity was seen between the fluid from isthmus or ampulla. Immunoaffinity column against bovine liver catalase, or direct addition of the antibody, did remove all catalase activities from the oviductal fluid. Purification of the oviductal fluid catalase was achieve by its elution from the immunoaffinity column. Indirect immunostaining of spermatozoa incubated in the oviductal fluid revealed a intense brown staining on the acrosomal cap.

Since $H_2O_2$ is a key product in the chain reaction of free radical production, this new enzyme could be the foremost important product of the female tract for sperm survival. Because this enzyme binds to spermatozoa, it could be use to protect the sperm cells when they are thaw up until they are used to fertilize.

Collection and Preparation of Oviductal Fluid

Oviducts from estrous, metestrous and proestrous cows (four of each) were transported from the slaughterhouse to the laboratory on ice, and dissected free from other tissues. Depending of the experiment, the isthmus was separated from the ampulla. Oviductal cells were extracted by compressing the oviducts with a glass slide and the mucosal tissue was rinsed in Tris-EDTA (40 mM, 1 mM) buffer. The cells were incubated twice for 30 min at 37° C. then centrifuged (10 min, 1500×g) and the supernatant reserved each time. The pooled supernatant (containing oviductal secretions only) was then centrifuged (15 min, 20 000×g) filtered (0.45 µm) and frozen for further experimentation. Four different pools were constituted.

Sperm Motility Analyses Following Incubation with Oviductal Fluid

Frozen semen, pooled from five bulls, was prepared and donated by the Centre d'Insémination Artificielle du Québec Inc. (C.I.A.Q. Inc., St-Hyacinthe, Québec, Canada). The same pool was used throughout the study. Straws were thawed in a water bath (35° C. for 60 sec) and the sperm were washed twice in Sp-Talp (Parrish J J et al., 1988, *Biol. Reprod.*, 38:1171–1180) containing 6 mg/ml BSA. Approximately 15 million spermatozoa (50 µl) were added to a pre-equilibrated solution composed of 225 µl Tris-EDTA containing 0.5 mg/ml OFP plus 225 µl TCM-PVP (TCM-199+3 mg/ml Polyvinylpyrolidone-360™ (PVP), Sigma) or control solution (225 µl Tris-EDTA containing 0.5 mg/ml PVP+225 µl TCM-199-PVP) for a final concentration of about 30 million sperm/ml. Tubes were mixed and incubated for 30 min (37° C., 5% $CO_2$) in a humidified incubator. Following this, tubes were centrifuged 5 min at 250×g, the supernatant removed and the pellet washed once more with 500 µl of TCM-PVP. The final pellet was dissolved in 500 µl TCM-PVP and the motility recorded as time 0. Sperm motility was then measured every 2 h for up to 6 h.

Sperm motility (i.e. percentage of motile sperm) was assessed with a Hamilton-Thorne Sperm Motility Analyzer™ (Hamilton-Thorne Research, Beverly, Mass.). For each tube, 2 thoroughly mixed aliquots (5 µl each) of sperm suspension were placed on a prewarmed MicroCell™ counting chamber (Conception Technologies, San Diego, Calif.). The chamber was then placed on the warmed stage (37.5° C.) of the motility analyzer and a minimum of 8 fields and 150 sperm were selected and scanned automatically by the analyzer for evaluation of motility. Slow cells (track speed (VCL) less than 20 µm/sec) were counted as immotile. Three independent binding-motility experiments were performed, with the same oviductal fluid batch.

Determination of the Catalase Activity in the Oviductal Fluid

Catalase activity in the oviductal fluid was assayed by the disappearance of $H_2O_2$ with a spectrophotometer. Briefly, 30% $H_2O_2$ (Sigma Chemical Company, St-Louis, Mo.) was dilute in 50 mM phosphate buffer until the absorbency at 240 nm ranged from 0.550 to 0.520. Fifty µl of oviductal fluid was then add to 950 µl of that solution, vortexed and the optical density was recorded at 15 sec and 1 min later. Dilution of oviductal fluid was performed as necessary to obtain similar decrease in optical density from one sample to and other. Knowing the protein concentration of each sample (Biorad) and that a 0.050 decrease at 240 nm correspond to the disappearance of 3.45 µmoles, total units of catalase activity per mg of protein in oviductal fluid was calculated. Each sample was assayed twice.

Purification of the Catalase Activity

Since a catalase activity was detected in oviductal fluid, a immunoaffinity column was prepared to purify this activity. Two mg of a purified IgG fraction from rabbit serum, directed against a catalase (from bovine liver; Biomol Research Laboratories Inc. Plymouth meeting, Calif.), was coupled to 3 ml of cyanogen bromide-activated sepharose beads (Pharmacia Biotech, Baie d'Urfé, Québec, Canada). Hundred fifty (150) ml of oviductal fluid were loaded onto the anti-catalase column and the beads were washed with 30 ml of PBS. Fractions of 1 ml were collected and the catalase activity in each tube was assay as previously describe. To elute the catalase activity from the column, 10 ml of 0.1 M glycine, pH 2.6, was loaded on the column. Fractions of 900 µl were collected and 100 µl of $Na_2HPO_4$ 0.5 M, pH 11.5 was added to the tube to neutralize the collected fraction. Catalase activity in each of the ten fractions was assay as describe previously.

Direct effect of the addition of an anti-catalase on the catalase activity in the oviductal fluid was also measured. Anti-catalase IgG was diluted at various concentration in oviductal fluid, and incubated for 90 min at 37° C. The residual catalase activity in the fluid was then assayed as described previously.

Immunodetection of Oviductal Fluid Catalase (OFC)

Proteins from bovine, porcine and human oviductal fluid, or human cervical mucus was precipated using the methanol-chloroform method. Briefly, 400 µl of MeOH was added to 100 µl of proteins solution and vortexed. After that, 100 µl of CHCl3 were added and vortexed. Then 300 µl of H2O were added, vortexed, and the tubes were centrifuged 2 min. at 10 000×g. The upper aquous phase was removed and discarded. Three hundred µl of MeOH were added to the remaining, vortexed and centrifuged 5 min. at 10 000×g. Tubes were decanted and air dry. Pellets were dissolved and boiled in SDS-blue buffer. Fractions were submit to one-dimensional SDS-PAGE electrophoresis. Electrophoretic patterns were stained with bromophenol blue or transfer on a nitrocellulose membrane.

Western blots were saturated overnight at 4° C. in PBS containing 5% (w/v) defatted milk. After three washes with 0.2% Tween 20 in PBS, the electrotransfers were incubated for 2 hrs with the anti-catalase (from bovine liver; Biomol) diluted 1:3000 in PBS. Before use, the antiserum was preadsorbed on a human keratin powder. After three washes with PBS-0.2% TWEEN™ 20, the nitrocellulose membrane were incubated at room temperature for 45 min with a peroxidase-conjugated anti-rabbit IgG diluted 1:3000 in PBS and washed three times with PBS-0.2% TWEEN™ 20. The immune complexes were detected using a BIOMAX™ film (Eastman Kodak, Rochester, N.Y.) after incubation with a chemiluminescent substrate of peroxidase as recommended by the supplier's instruction (ECL™ kit: Amersham, Buckhinghamshire, UK).

Immunostaining of Oviductal Fluid Catalase Bound to Bovine Spermatozoa

Frozen semen from the same pool was thawed as before and the sperm were washed twice in PBS buffer (0.02% KCl, 0.02% $KH_2PO_4$, 0.11% $Na_2HPO_4$, 0.01% $CaCl_2$, 0.01% $MgCl_2$, 0.8% NaCl, 0.1% BSA) containing 6 mg/ml BSA (Fraction V, Sigma Chemicals, St-Louis, Mo.). Ten µl of freshly washed sperm (150 million/ml) were added to 45 µl of oviductal fluid, and 45 µl of TBS buffer (10 mM Tris, 150 mM NaCl) with 3.5 mM $CaCl_2$, for a final calcium concentration of 1.5 mM The preparation (final volume=100 µl) was then mixed and incubated for 30 min at 38.5° C. Following incubation, tubes were centrifuged 10 min at 400×g, the supernatant removed and the pellet washed 3 more times with 0.5 ml of PBS. Spermatozoa were smeared onto microscope slides and air dried.

Determination of catalase presence at sperm surface was done by indirect immunostaining. Antigen localization was performed by the avidin-biotin peroxidase staining procedure using the Vectastain ABC™ kit (Vector Labs, Burlingame, Calif.). Nonspecific staining was avoided by a 1-h preincubation of the spermatozoa fixed slides with 10% (v:v) goat serum in PBS (pH 7.4) followed by three washes in PBS. Slides were incubated for 2 h with a rabbit (IgG fraction) anti-catalase from bovine liver (Biomol). The antibody was used at a dilution of 1/1000 in PBS. After three washes with PBS, slides were treated for 30 min with goat biotinylated anti-rabbit IgG (Sigma) diluted 1/100 in PBS, washed three times in PBS, and then incubated for 30 min with Vectastain ABC™ reagent. After three washes in PBS, spermatozoa were revealed with peroxidase substrate (0.118 M aminoethyl carbazol (Sigma) in 100 mM sodium acetate buffer, pH 5.2) in the presence of 0.002% $H_2O_2$ for exactly 10 min. Slides were washed in water and counterstained with Harris hematoxylin (Sigma, ACCUSTAIN™), fixed with a 5% acetic acid solution, washed extensively in water, and finally mounted with DAKO GLYCERGEL™ (Dako Corp., Carpiteria, Calif.) under coverslip. Great care was taken in order to proceed all samples the same manner. They were all treated in parallel in order to avoid technical variability and to allow comparison of staining from one sperm sample to the other.

Radio-Iodination of the Purified Oviductal Fluid Catalase (OFC)

Purified oviductal fluid catalase from immunoaffinity column was labeled with $^{125}I$. Briefly, 10 µl of Chloramine-T (0.05 mg/ml PBS) was added to 10 µl of iodination buffer (0.3 M NaPO4 pH 7.5; IB) 10 µl OFC (0.5 mg/ml IB) and 10 µl of $NaI^{-125}$ (1 mCi in IB) for 5 min. The reaction was stopped by adding 1 ml of PBS. The sample was then eluted with PBS+0.1% BSA on a 25 $ml^3$ SEPHADEX™ G-75 fine column to remove labeled OFC from free $I^{-125}$. Radioactive fractions were pooled and frozen until use.

Binding of $^{125}I$-OFC to Sperm Membranes

Frozen semen, pooled from five bulls, fresh pig semen, or uterine mouse cell (as negative control) were washed twice in in PBS buffer (0.02% KCl, 0.02% $KH_2PO_4$, 0.11% $Na_2HPO_4$, 0.03% $CaCl_2$, 0.01% $MgCl_2$, 0.8% NaCl, 0.1% BSA). Twenty µl of the cell suspension (200 million/ml) were added to 20 µl of the labeled OFC (~600 000 cpm), and 70 µl of PBS buffer. The preparation was then mixed and incubated for 30 min at 37° C. Following incubation, tubes were centrifuged 10 min at 400×g, the supernatant removed and the pellet washed 3 more times with 1 ml of PBS, changing the tube each wash. The final pellet of cells was dissolved and boiled in 110 µl of SDS-blue buffer and 10 µl was counted with a gamma counter (LKB 1261 Multigamma, Pharmacia-LKB, Baie d'Urfé, Qc, Canada). The remaining volume was submitted to gel electrophoresis (see below).

One-Dimensional Gel Electrophoresis and Autoradiography

Solubilized sperm, precipitated labeled OFP were separated using one-dimensional SDS-PAGE and a continuous buffer. Resolving gels were cast using 12% acrylamide; stacking gels contained 4% acrylamide. Polymerization of gels was induced by addition of 5% ammonium persulfate. A measured volume of labeled OFP bound to sperm samples (1000–2000 cpm) were loaded on gels. Molecular weight $^{14}C$-methylated protein standards were lysozyme, 14.3 kDa; carbonic anhydrase, 30 kDa; egg albumin, 46 kDa; bovine serum albumin (BSA), 66 kDa; phosphorylase-b, 97.4 kDa; and myosin, 220 kDa (Amersham, Oakville, ON.)

After electrophoresis, gels were dried at 80° C. in a slab gel dryer (Biorad, Model 543, Missisauga, ON) between two sheets of porous membrane. Dried gels were placed in a KODAK™ X-ray exposure holder with KODAK X-OMAT™ XAR-5 film and an intensifying screen, and stored at −80° C. for 5–10 days. Films were processed with a KODAK X-OMAT™ automatic developer.

Effect of the Binding of OFP on the Maintenance of Sperm Motility

Figure 1:
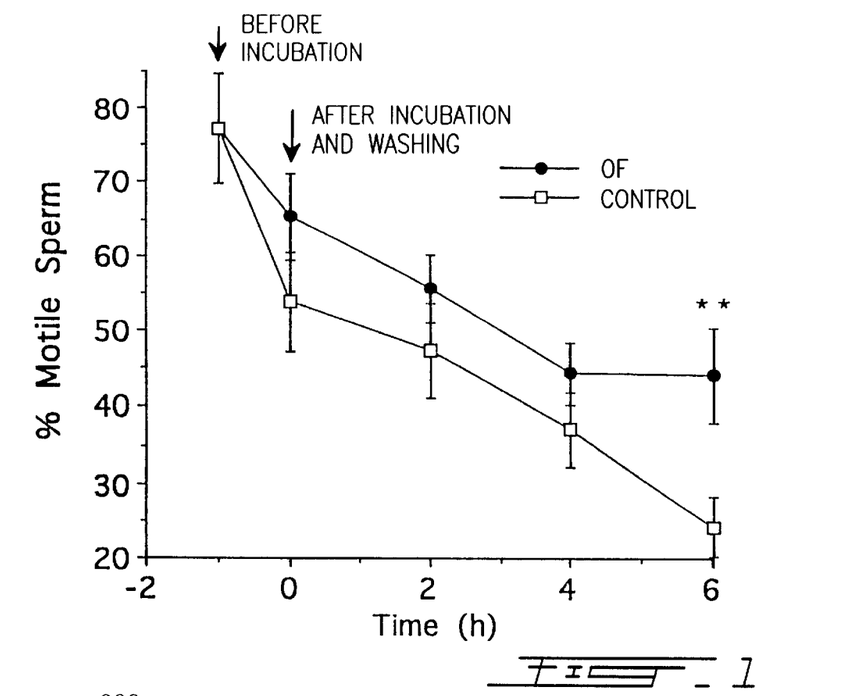
FIG. 1 is a graph of sperm motility measurements following preincubation with bovine oviductal fluid (OF)

FIG. 1 represent a graph of sperm motility measurements following preincubation with oviductal fluid (OF). Freshly washed sperm were preincubated in the presence or absence of OF, washed then incubated for 6 h in TCM-199. The motility was then recorded with a Hamilton-Thorne motility analyzer. Results are means (±SEM) of 3 independent experiments (** P<0.01; FIG. 1).

Since only some proteins from OF bind to sperm membranes, this experiment was performed to investigate whether this binding affects the maintenance of sperm motility. This figure shows that after a short 30 min incubation in presence of calcium and one wash, survival was better in presence of oviductal fluid (time 0). This difference is not significant compare to control for the first 4 h (P>0.5), but this trend was maintained through 6 h, at which time the percentage of motile sperm incubated in control media dropped dramatically (23.8%±5.7) whereas that of sperm incubated with OF remained at a higher level (44.2%±6.3, P<0.01). These data suggest a possible association between binding of specific proteins to sperm and the subsequent prolongation of sperm viability.

Catalase Activity in the Oviduct

In culture medium containing specific amino acids, high $H_2O_2$ concentration are present. Since this negative effect could be eliminated by in vitro oviductal secretions, or only by a preincubation of sperm in oviductal fluid (FIG. 1), we suspected a catalase activity in bovine oviductal fluid.

Figure 2:
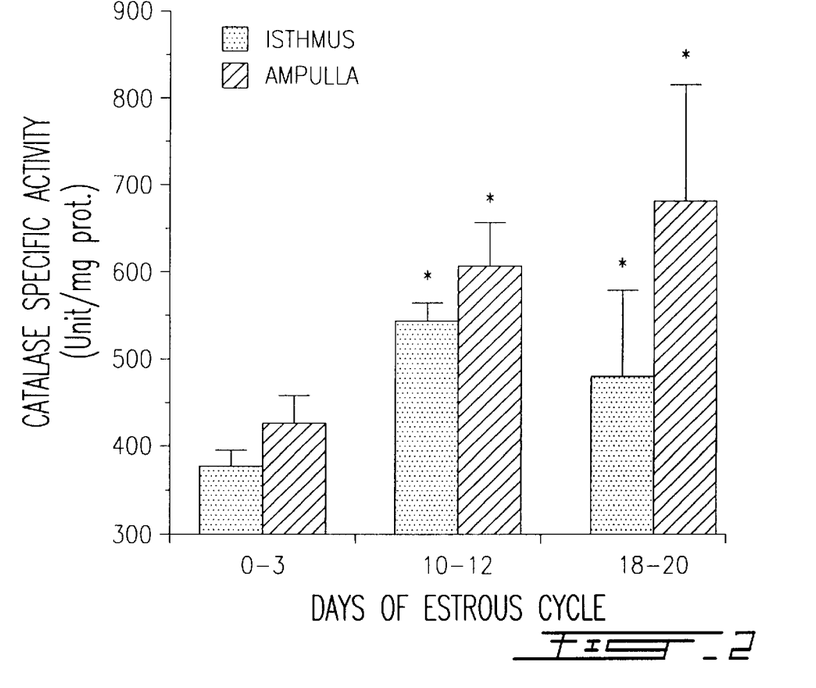
FIG. 2 is a graph of assay of the catalase activity found in the bovine oviductal fluid.

The presence of a catalase activity in that fluid is shown in FIG. 2. Tubal cells were harvested and washed to obtain the fluid. Determination of the catalase activity was measured twice by the diparition of $H_2O_2$ at 240 nm with a spectrophotometer. Results are means (±SEM) of 4 independent experiments (* P<0.05 from days 0–3; FIG. 2).

Catalase specific activity increased in the fluid during the estrous cycle, to reach maximal activity just before ovulation (days 18–20). Fluid from pre-ovulatory oviduct showed large variations in the catalase specific activity. In two experiments the level were as low a fluid from day 0–3, while in two others experiments the catalase specific activity was twice superior. Although the catalase activity in the ampulla was always above than the isthmus, this difference was not significant (P=0.081).

Neutralization of the Catalase Activity

To further prove the presence of a catalase activity in the bovine oviductal fluid, a purified IgG fraction from rabbit serum, directed against a catalase from bovine liver, was used to neutralize the oviductal catalase activity. A immunoaffinity column coupled with the anti-catalase removed 100% of the original catalase activity found in the fluid. Direct addition of the antibody in the oviductal fluid also removed the activity in a dose dependent-manner, as seen in Table 1.

TABLE 1

Effect of the addition of an anti-catalase on the catalase activity in the oviductal fluid

| Antibody added | Residual catalase activity |
| --- | --- |
| None | 100% |
| 1/1000 | 31% |
| 1/500 | 22% |
| 1/300 | 14% |

TABLE 1-continued

Effect of the addition of an anti-catalase on the catalase activity in the oviductal fluid

| Antibody added | Residual catalase activity |
| --- | --- |
| 1/200 | 9% |
| 1/100 | 6% |

Purified IgG fraction from rabbit serum, directed against a catalase from bovine liver, was diluted at various concentration, and incubated for 90 min at 37° C. The residual catalase activity in the oviductal fluid was then assayed as described above.

Purification of the Catalase Activity

Immunoaffinity purification of the oviductal catalase activity was successfull. Fractions eluted from the column were highly active, while no activity remained in the oviductal fluid passed through the column. The purify fraction showed a single band in the 60 kDa area on SDS page electrophoresis under denaturing conditions (bromophenol blue coloration).

Immunodetection of Oviductal Fluid Catalase

Figure 3:
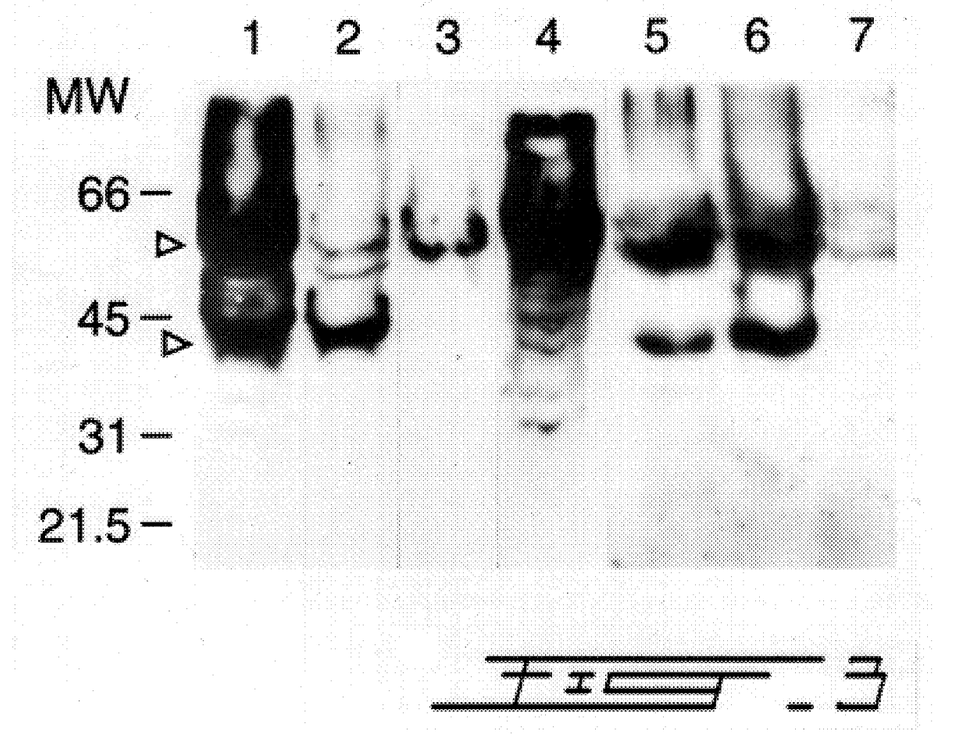
FIG. 3 illustrates the immunodetection of oviductal fluid catalase (OFC) in bovine, porcine and human oviductal fluid.

As seen in FIG. 3, two major bands at 60 and 40 kDa, were detected by Western blot in bovine oviductal fluid (open arrow head; lane 1). The 60 kDa band does not appear in lane 2 representing oviductal fluid, passed through the immunoaffinity column, without catalase activity. Lanes 3 and 4, represent respectively 10 and 100 μl of the purify catalase fraction eluted from the immunoaffinity column. The presence of the 60 kDa band can also be seen in porcine oviductal fluid (lane 5), human oviductal fluid (lane 6) and human cervical mucus (lane 7), and correlate with the catalase activity also found in these three fractions.

Immunostaining of Oviductal Fluid Catalase Bound to Bovine Spermatozoa

The results presented in FIG. 1 suggested a possible association between binding of specific proteins to sperm and the subsequent prolongation of sperm viability. To verify that this effect could be due to the binding of a catalase from the oviductal fluid, an immunoperoxidase staining of the spermatozoa incubated with the fluid, probed with the anti-catalase was performed.

Figure 4A:
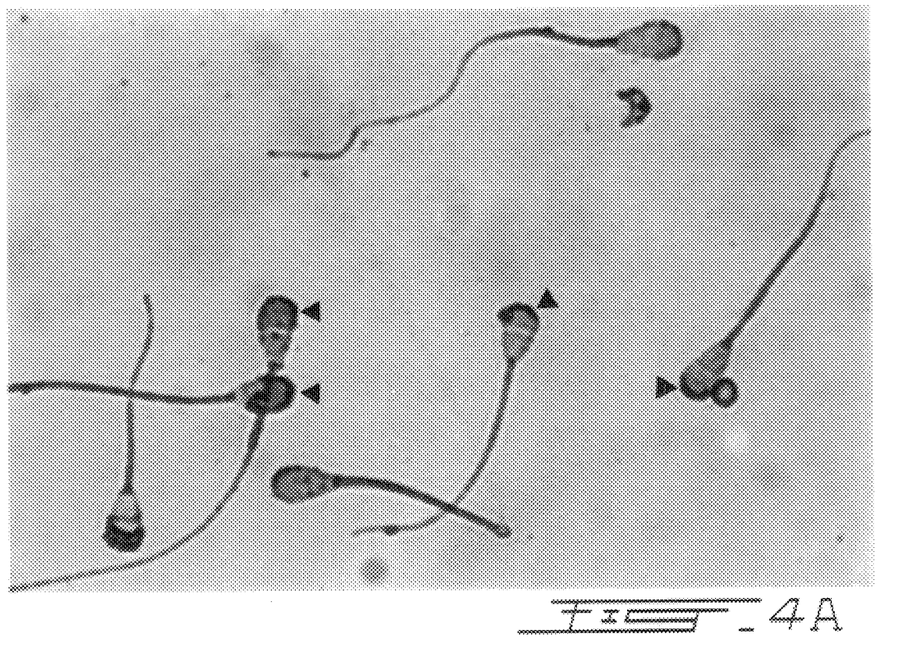
FIGS. 4A to 4D illustrate the binding of OFC to bovine sperm.
Figure 4B:
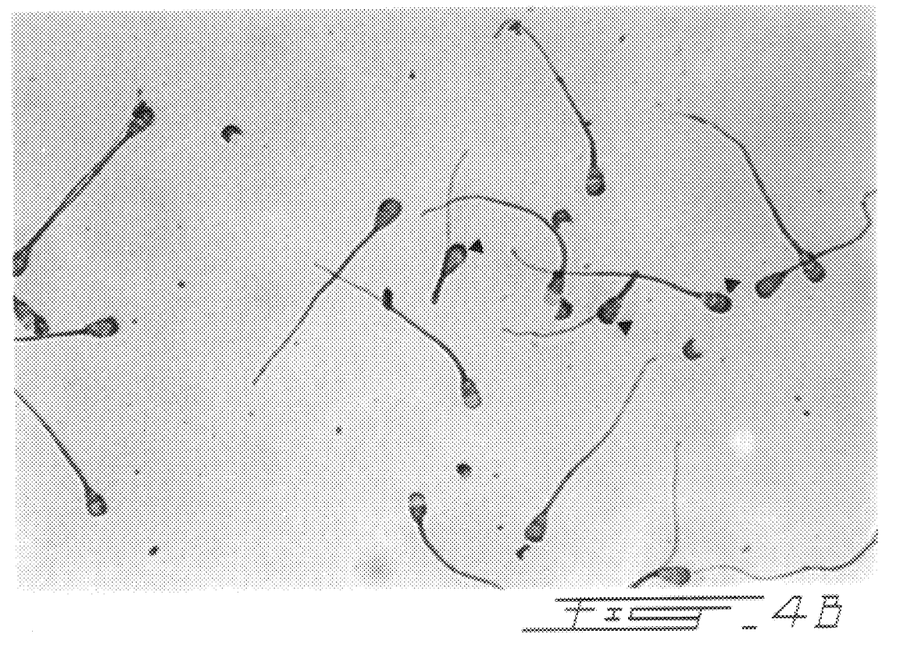
Figure 4C:
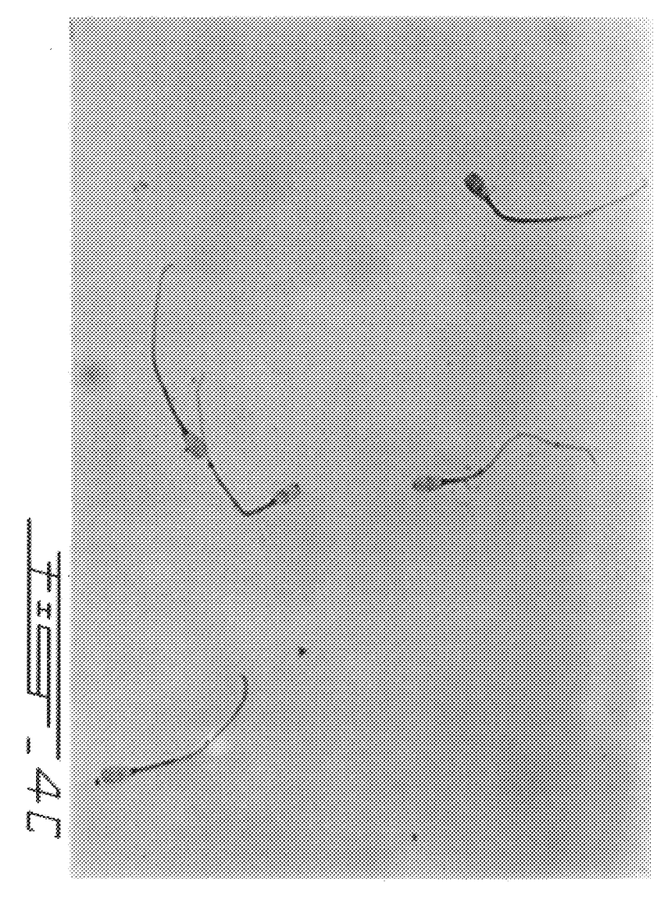
Figure 4D:
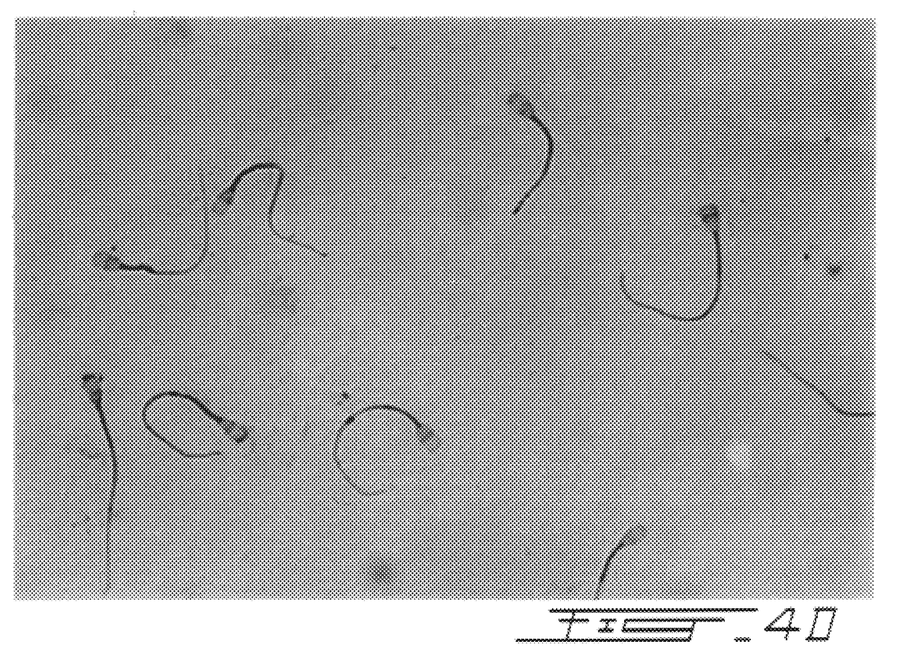

Spermatozoa incubated in the oviductal showed an intense brown staining of the acrosomal cap as illustrated by arrow heads in FIG. 4A (400×) and FIG. 4B (200×). Spermatozoa incubated with catalase from bovine liver (FIG. 4C; 200×) or in PBS alone (FIG. 4D; 200×) did not show any staining, and their acrosome remained blue. Those results clearly shows a specific binding of the catalase from the oviductal fluid with the spermatozoa while no such binding occurs when catalase from other sources was used.

Binding of $^{125}$I-OFC to Sperm Membranes

Figure 5:
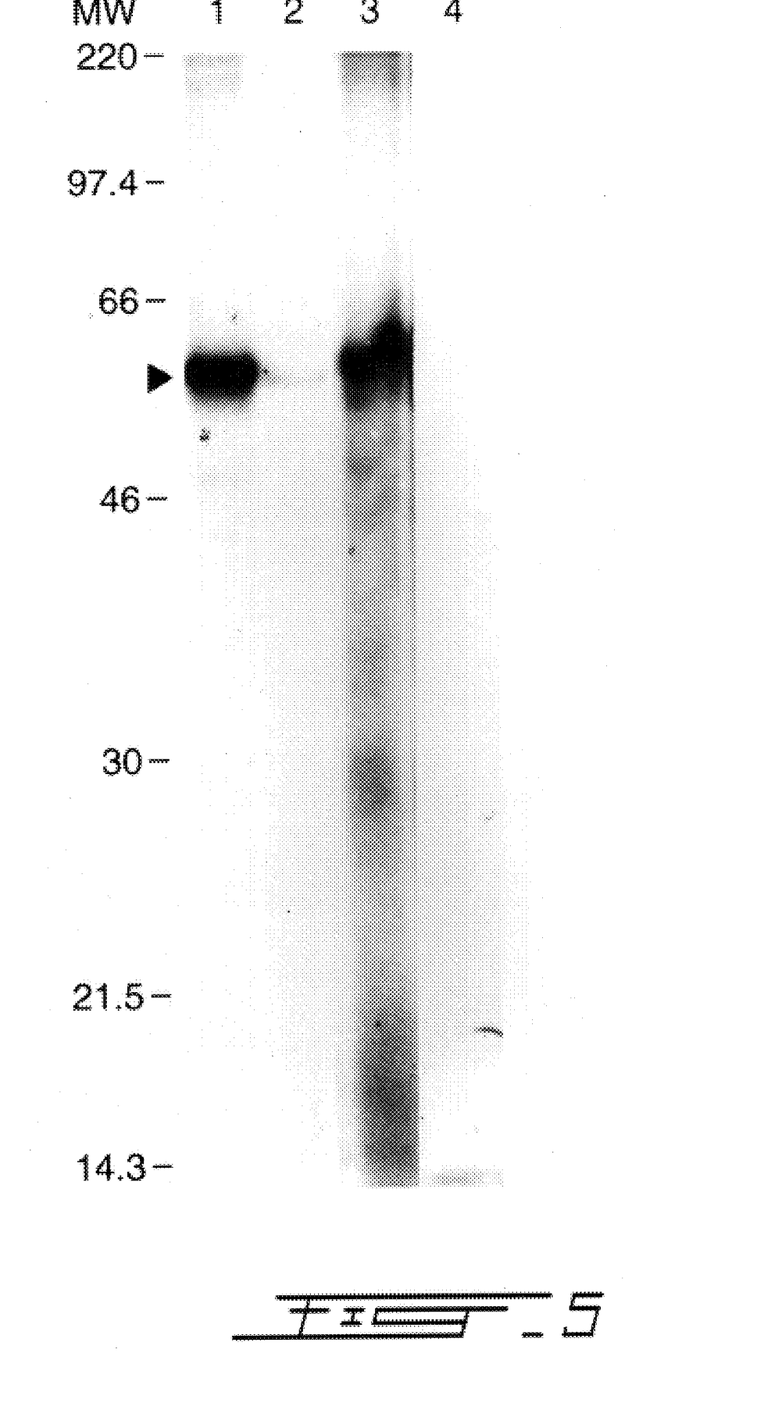
FIG. 5 illustrates the binding of bovine $^{125}$I-OFC to bovine and porcine sperm membranes.

FIG. 5 shows the specific binding of $^{125}$I-OFC to bovine and porcine sperm. As seen in Lane 1, only one major band is visible in the 60 kDa area, showing a high degree of purity of the fractions eluted from the immunoaffinity column. Bovine and porcine spermatozoa incubated in presence of the labeled OFC did bind the protein to their surface. However, mouse uterine cells (used as a negative control) did not bind the protein which demonstrate a specific binding of the OFC only to sperm surface.

Discussion

Only a few studies have demonstrated the binding of oviductal proteins to the sperm of mammalian species, including human, ram, stallion, and bull. As reproduce in FIG. 1, we have previously reported that the binding of oviductal fluid proteins to the sperm membrane had a positive effect on sperm survival in TCM-199 medium. However at that time, the exact mechanism of action of those proteins was not completely understood. The current results clarify the situation and shows for the first time a potential function of the bound proteins.

Catalase has been purified from plants, bacteria, fungi, and mammalian liver and blood. Catalases from these sources show a high degree of similarity. They have a relative molecular weight in the range of 225,000 to 270,000, contain four equally sized subunits, with each possessing a ferric heme. We report here, for the first time, the presence of a catalase secreted by the mammalian oviduct. Specific catalase activity was found to increase in the oviductal fluid to the approach of the ovulation and no significant difference was found between the isthmus and the ampulla (FIG. 2). The presence of such an enzyme in the female genital tract is an outstanding discovery since $H_2O_2$ is highly toxic for bovine sperm. $H_2O_2$ not only inhibit the motility, but also the acrosome reaction, the sperm binding with the egg and oocyte penetration. Furthermore, the decomposition of $H_2O_2$ breaks the chain reaction of free radical production which leads to lipid peroxidation. It has been calculated that this process could be the limiting factor of the lifetime of mammalian spermatozoa in the oviduct (Alvarez J G et al., 1987, *J. Androl.,* 8:338–348). It is therefore tempting to speculate that this new enzyme is the foremost important product of the female tract for sperm survival.

Binding of spermatozoa to oviductal cells has been demonstrated in many species. This binding appears to be important as for the survival than for the capacitation of the spermatozoa. During that process, spermatozoa acquire at their surface material produced by the oviductal cells. Here, we showed that the catalase secreted by the oviduct also binds the membrane of the spermatozoa. It's the first time it is been shown that such an enzyme interacts so closely with mammalian sperm. In vivo studies showed that, before ovulation, spermatozoa interact with oviductal cells by their rostral surface, and that oviductal surface-coating material is distributed predominantly over the anterior portion of the sperm head. These observations are in agreement with our results, and support the role of the oviduct as a sperm storage site since elimination of $H_2O_2$ from sperm environment can only have beneficial effect. The coating of sperm with an oviductal catalase thus offers a maximal protection. A different method also showed that specific binding of the oviductal fluid catalase occur to bovine and also porcine sperm (FIG. 5)

In summary, we report for the first time the presence of a catalase in the bovine oviductal fluid. Specific activity of this enzyme increased at the near the ovulation. Furthermore, oviductal catalase, which can be purify by immunoaffinity, appears to bind on the acrosomal cap of the spermatozoa. Since $H_2O_2$ is a key product in the chain reaction of free radical production which led to lipid peroxidation, this new enzyme could be the foremost important product of the female tract for sperm survival.

The enzyme complete characterisation is presently in process. These will includes: determination of native molecular weight and pI, partial amino acid sequence (chemical procedures) and complete sequence via cloning of the gene.

Different Uses of the Oviductal Catalase of the Present Invention

Addition of that enzyme could greatly improve fertility rates with low sperm concentration in artificial insemination. Hydrogen peroxide ($H_2O_2$) is a highly reactive oxygen species which is one of the most toxic compound to sperm. In the uterine cavity, a lot of leukocytes are found at estrous time, and those cells produce large quantities of $H_2O_2$. Moreover, our laboratory has recently shown that specific amino acids (AA) stimulated the production of hydrogen peroxide by dead spermatozoa. Since those AA are found in the bovine uterus as well than the oviduct, $H_2O_2$ could be a major player in the death of sperm in the female genital tract. In fact, Alvarez et al. calculated that lipid peroxidation (due to the presence of free radicals) is the limiting factor for the lifetime of mammalian spermatozoa in the oviduct (Alvarez J G et al., 1987, *J. Androl.,* 8:338–348). Spermatozoa coated with catalase could therefore be much more resistant to $H_2O_2$ found in the uterus, site where semen is deposited during AI procedure. Moreover, this catalase could not only protect sperm that are alive after thawing, but, by coating the sperm, stabilize the membrane and improve survival during migration in the uterus.

If more sperm can make it to the oviduct, the number of sperm present in one straw could be seriously reduced. This option would allow to make more straws with the same ejaculate and therefore increase the sales for a bull in high demand. An other option is a "long range semen". Addition of the catalase to the semen could increase the insemination window from 1 day to 2 days.

Relation between the binding of oviductal catalase and fertility has not been investigated yet. It is possible that, as in the capacity of the spermatozoa to bind with the oviductal cells, there are differences between bulls. In which case, the binding of the catalase with the sperm could be a screening test helpful in the insemination industry. Semen from potential low fertility bulls could be screened form the start, and correction could be applied in the extender. Measurement could be made by the flow cytometer using labeled antibody against catalase following a short preincubation in medium containing the oviductal catalase.

The bovine AI industry may not be the only one to take advantage of that discovery since a similar product has been detected in oviductal fluid of the sow (FIG. 3). Boar semen is extremely affected by the freeze-thaw procedure because sperm membranes are a lot more sensitive than bull. As proposed previously, spermatozoa coated with such catalase, could have their membrane stabilized and exhibit higher survival rates during normal conservation at 16° C. or during freeze-thaw procedure.

This catalase could also be advantageous to detect and/or solve some human infertility problems. As proposed for bulls, it is possible that there is an incapacity for spermatozoa from infertile man to bind the catalase. In such case, a screening test could be performed to avoid clinical procedures that cannot overcome the inability of the spermatozoa to survive in the female tract. Addition of purified catalase to semen of patient with very low sperm count, during the swim-up procedure, could increase fertility by preserving the viability of those precious spermatozoa. It is also possible that in some case, that the catalase in not produced by the female genital tract. In such circumstance, pre-treatment of the semen in vitro with purified catalase before insemination, or insertion of a capsule of catalase in the vagina of the women, before the sexual relation, could correct that infertility problem.

Those applications are only some of the possibilities with such a product.

The present invention will be more readily understood by referring to the following examples which are given to illustrate the invention rather than to limit its scope.

EXAMPLE I

Detection of Low Fertility or Fertility on Male Subject

Semen from any species is manipulated as described in section: Immunostaining of oviductal fluid catalase bound to bovine spermatozoa. Detection of a intense brown staining on the acrosomal cap (see FIGS. 4A, 4B) signify a normal and fertile subject. However, the absence of a brown coloration on spermatozoa surfaces (such as FIG. 4D) suggest an inability for spermatozoa to bind the OFC, caused by the absence of a binding site, and a infertility problem. With the use of a specific antibody directed against the OFC binding site it will be possible to detect directly the presence of the binding site by using the same principle as in the methods described in the sections: Immunodetection of Oviductal Fluid Catalase (OFC) and Immunostaining of oviductal fluid catalase bound to bovine spermatozoa.

EXAMPLE II

Detection of the Presence of Catalase in Female Cervical Mucus

Cervical mucus is collected by gynecologist. Equal volume of PBS buffer is mixed to the mucus, incubated for 30 min. at 37° C. and centrifuged 10 min. at 10 000×g. Catalase activity in the supernatant is then measure directly by spectrophotometry, or indirectly by immunodetection. Detailed description of the method to measurement of the catalase activity and presence is mentioned below (Determination of catalase activity in oviductal fluid; Immunodetection of Oviductal Fluid Catalase (OFC)).

EXAMPLE III

Methods for Improving Spermatozoa Survival

A) In Semen Extenders

The purified catalase of the present invention (OFC) is added to the semen extenders destined to crypreservation or fresh semen conservation before sperm addition. Protective effects starts immediately by removing toxic $H_2O_2$ from the solution and continue in the presence of spermatozoa. For semen destined to cryopreservation, allow 30–60 min. at room temperature before freezing to permit to the OFC to interact and bind to the spermatozoa membranes.

B) For Spermatozoa Destined to Artificial Insemination

Purify OFC is added to the swim-up buffer and/or the washing buffer before sperm addition. Protective effects starts immediately by removing toxic H2O2 from the solution and continue in the presence of spermatozoa. Purify OFC is also present in the resuspending medium to be use for artificial insemination.

C) Insertion of a Capsule Containing OFC in the Vagina Before Coït

Purify OFC can be inserted in porous capsules membranes such as poly-lysine or collagen. The capsule is then inserted in the women vagina 30–60 min. before coït. Semen deposited later on, will interact with the liberated OFC and spermatozoa will benefit from the presence of OFC to their surface.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An in vitro method for improving spermatozoa survival during migration in oviduct and/or uterus for artificial insemination; which comprises the steps of isolating spermatozoa from a male subject; and coating the isolated spermatozoa with an isolated oviductal catalase enzyme.

2. The method of claim 1, wherein the catalase enzyme is isolated from a biological source or is recombinantly produced.

3. The method of claim 1, wherein the isolated oviductal catalase enzyme is isolated from oviduct selected from the group consisting of human oviduct, bovine oviduct, caprine oviduct, equine oviduct, ovine oviduct, and porcine oviduct.

4. The method of claim 1, wherein the isolated spermatozoa is selected from the group consisting of isolated bovine spermatozoa, isolated caprine spermatozoa, isolated equine spermatozoa, isolated ovine spermatozoa, isolated porcine spermatozoa, isolated canine spermatozoa, isolated feline spermatozoa, isolated primate spermatozoa, isolated pachyderm spermatozoa and isolated human spermatozoa.

5. A composition of spermatozoa for artificial insemination with stabilized spermatozoa membrane and improved spermatozoa survival during migration in oviduct and/or uterus, wherein said composition comprises isolated spermatozoa coated with an exogenous isolated oviductal catalase enzyme.

6. The composition of claim 5, which further comprises an agent preventing lipid peroxidation.

7. The composition of claim 5, wherein said coated isolated spermatozoa is frozen.

8. The composition of claim 5, wherein the exogenous isolated oviductal catalase enzyme is isolated from oviduct selected from the group consisting of human oviduct, bovine oviduct, caprine oviduct, equine oviduct, ovine oviduct and porcine oviduct.

9. The composition of claim 6, wherein the agent preventing lipid peroxidation is selected from the group consisting of Vitamin E (α-tocopherol), Vitamin C (ascorbic acid), pyruvate, glutathion, uric acid, taurine, albumine, DMSO, superoxid dismutase (SOD), catalase and lactoferrin.

10. The composition of claim 5, wherein the isolated spermatozoa is selected from the group consisting of isolated bovine spermatozoa, isolated caprine spermatozoa, isolated equine spermatozoa, isolated ovine spermatozoa, isolated porcine spermatozoa, isolated canine spermatozoa, isolated feline spermatozoa, isolated primate spermatozoa, isolated pachyderm spermatozoa and isolated human spermatozoa.

* * * * *